United States Patent
Ostertag

(10) Patent No.: US 8,454,782 B2
(45) Date of Patent: Jun. 4, 2013

(54) METHOD OF FORMING AN ABSORBING DISPOSABLE INCONTINENCE DIAPER

(75) Inventor: Wolfgang Ostertag, Gerstetten (DE)

(73) Assignee: Paul Hartmann AG, Heidenheim (DE)

( * ) Notice: Subject to any disclaimer, the term of this patent is extended or adjusted under 35 U.S.C. 154(b) by 141 days.

(21) Appl. No.: 12/737,856

(22) PCT Filed: Sep. 5, 2009

(86) PCT No.: PCT/EP2009/006460
§ 371 (c)(1),
(2), (4) Date: Feb. 23, 2011

(87) PCT Pub. No.: WO2010/028786
PCT Pub. Date: Mar. 18, 2010

(65) Prior Publication Data
US 2011/0146892 A1      Jun. 23, 2011

(30) Foreign Application Priority Data
Sep. 9, 2008   (DE) .......................... 10 2008 046 358

(51) Int. Cl.
*A61F 13/493*   (2006.01)

(52) U.S. Cl.
USPC ........... 156/204; 156/264; 156/267; 156/269; 604/385.23; 604/391

(58) Field of Classification Search
None
See application file for complete search history.

(56) References Cited

U.S. PATENT DOCUMENTS

| 6,730,188 | B2 | 5/2004 | Sanders |
| 7,407,557 | B2 | 8/2008 | Wada |
| 2002/0148557 | A1 | 10/2002 | Heller |
| 2006/0244166 | A1 | 11/2006 | Wada |
| 2006/0271004 | A1* | 11/2006 | Petersen ................. 604/372 |
| 2007/0112321 | A1* | 5/2007 | Goates et al. ........... 604/389 |
| 2007/0142808 | A1 | 6/2007 | Wada |
| 2009/0198205 | A1* | 8/2009 | Malowaniec et al. .... 604/385.23 |

FOREIGN PATENT DOCUMENTS

| DE | 603 00 821 | 11/2005 |
| DE | 10 2005 048 868 | 4/2007 |
| EP | 1 269 949 | 1/2003 |
| EP | 1 504 738 | 2/2005 |

(Continued)

*Primary Examiner* — Barbara J Musser
(74) *Attorney, Agent, or Firm* — Paul Vincent

(57) ABSTRACT

The present invention relates to a process for producing a disposable diaper by supplying a continuous web of flat material in a longitudinal direction for the forming of the side portions, forming first material clearances along a first cutting line at a side edge) of the web of flat material to produce contoured cutouts in the web of flat material, an imaginary parallel line PL, which is parallel to the longitudinal direction and placed at the point P of maximum extent of the cutout transversely in relation to the longitudinal direction, defining an outer sub-region and an inner sub-region of the web of flat material, folding the web of flat material about at least one first folding line running in the longitudinal direction, the folding line running within the outer sub-region, severing longitudinal portions of the folded web of flat material, undetachably fixing the portions of material to a respective longitudinal edge of a web for the main part of the diaper for the forming of side portions, forming second material clearances along a second cutting line, the second cutting line taking in the side portions and a respective longitudinal edge of the web for the main part of the diaper, and the second cutting line crossing the first cutting line in such a way that the second cutting line does not extend through the first folding line of the front and rear side portions.

17 Claims, 5 Drawing Sheets

FOREIGN PATENT DOCUMENTS

| | | |
|---|---|---|
| EP | 1 574 191 | 9/2005 |
| EP | 1 719 484 | 11/2006 |
| EP | 2 020 215 | 2/2009 |
| WO | WO 03/082168 | 10/2003 |
| WO | WO 03/094815 | 11/2003 |
| WO | WO 2007/042084 | 4/2007 |

* cited by examiner

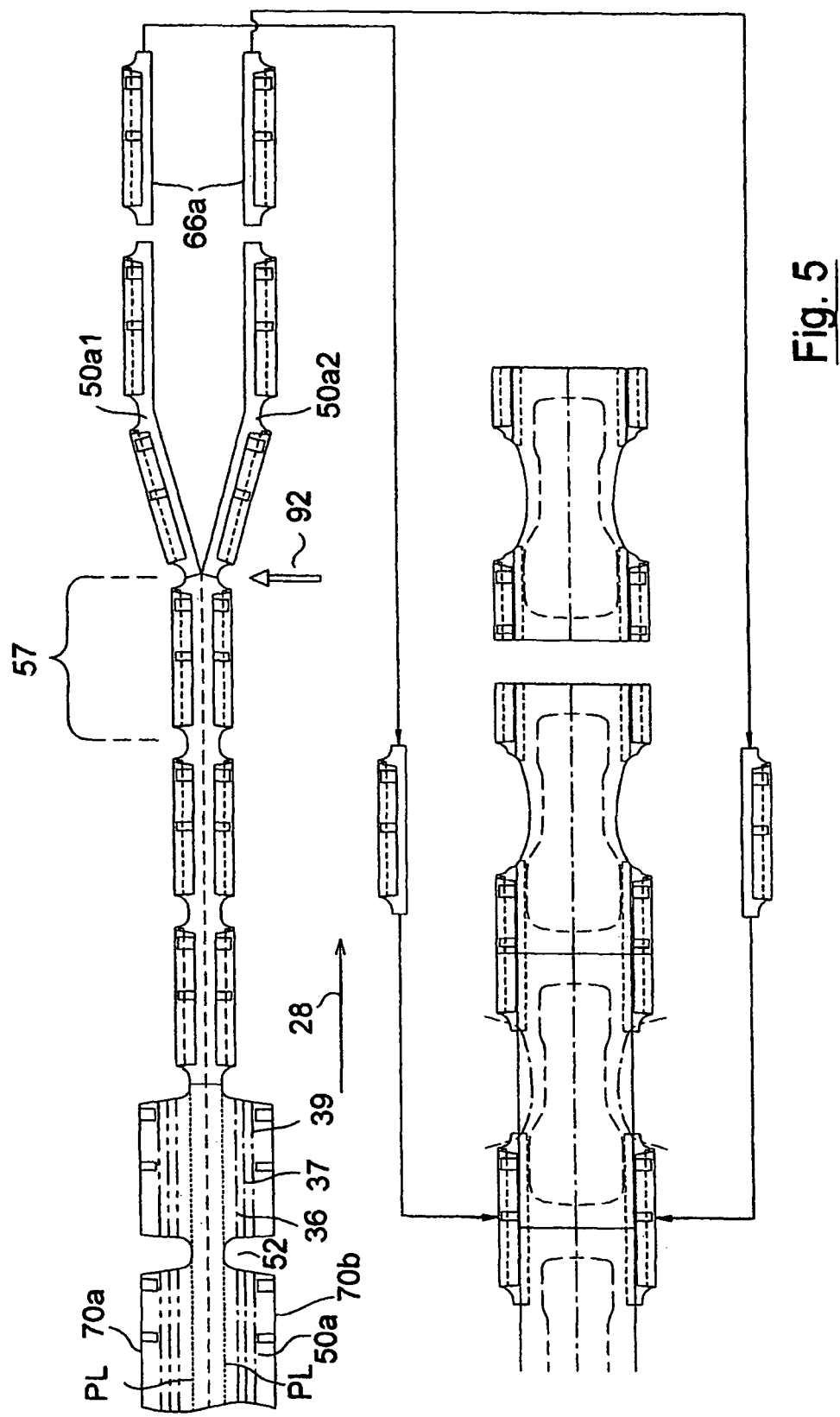

METHOD OF FORMING AN ABSORBING DISPOSABLE INCONTINENCE DIAPER

This application is the national stage of PCT/EP2009/006460 filed on Sep. 5, 2009 and claims Paris Convention Priority to DE 10 2008 046 358.2 filed Sep. 9, 2008.

BACKGROUND OF THE INVENTION

The present invention relates to the production of a disposable absorbent incontinence diaper of the open type with a main part comprising a front region, a rear region and a crotch region, lying in between in the longitudinal direction and coming to lie between the legs of a user, the main part comprising an absorbent pad, and with rear side portions, joined to the rear region on both sides, and front side portions, joined to the front region on both sides. The disposable incontinence diaper is envisaged for adults and intended to be used only once.

Disposable incontinence diapers of this type are known, for example, from DE102005048868A1. DE102005048868A1 also already discloses a different design of the side portions, to be specific providing the rear side portions with greater stretchability than the front side portions.

In the case of disposable incontinence diapers of this type, the mentioned side portions are often formed from a different material than the main part. For example, the side portions, which are often also referred to as "ears" of the disposable incontinence diaper, may be formed such that they are breathable, in particular permeable to air and water vapor, whereas the main part, which is often also referred to as the chassis, may be made impermeable to liquid. For closing the disposable incontinence diaper on the user, the side portions, which are preferably undetachably joined onto the rear region, are folded forward, in particular to the stomach side of the user, and detachably connected there either to the outer side of the front region of the main part or to the outer side of the side portions of the front region in an overlapping configuration.

As DE102005048868A1 shows, both the main part and the side portions of disposable incontinence diapers of this type respectively have a rectangular shape. DE102004021353A1, too, discloses a disposable incontinence diaper of this type. DE102004021353A1 also teaches pre-folding of the side portions and securing the pre-folding before use by detachable fixing. On high-speed diaper machines, a pre-folding of the side portions preferably also takes place before the fixing of the side portions to the main part of the diaper, so side portions that are already pre-folded and pre-fixed in this configuration are preferably joined onto the main part of the diaper. Even though this incontinence diaper can also be produced at high speeds, and consequently very cost-effectively, and the pre-folded side portions can preferably be opened with one pull, the wearing comfort of the already known disposable incontinence diapers is found to be unsatisfactory.

To solve this problem, it has already been proposed by DE102007056126 (still unpublished) to form the side portions as running obliquely in relation to the longitudinal direction, or in a curve-shaped manner, at least on their edges facing the crotch region, in order to form leg opening regions, and to form the main part in an hourglass-shaped manner, at least in the crotch region, the oblique or curve-shaped profile of the side portions and the hourglass-shaped contouring of the main part being formed on both longitudinal sides of the disposable incontinence diaper by a respective single severing operation, taking in the side portions and the main part. According to this concept, the severing operation taking in the side portions and the main part therefore takes place at a point in time at which the front and rear side portions are already joined onto the main portion. This ensures that the leg opening contouring of the side portions continues as it were unvaryingly in the crotch region of the main part, in order to form the hourglass-shaped contouring of the main part there.

The technical challenges in terms of the process for producing incontinence articles of this type on high-speed diaper machines are significant, however, since it is only with difficulty that the incontinence articles with the far-extending side portions can be stably conveyed through the high-speed diaper machine, and the required precision of the severing operation producing the leg opening regions can only be ensured with difficulty.

SUMMARY OF THE INVENTION

To solve this problem, a process is proposed for producing incontinence diapers of the open type with a main part comprising a front region with front lateral longitudinal edges, a rear region with rear lateral longitudinal edges and a crotch region, lying in between in the longitudinal direction and coming to lie between the legs of a user, the main part comprising an absorbent pad, and with rear side portions, joined to the rear region on both sides, and front side portions, joined to the front region on both sides, extending in the transverse direction beyond the lateral front and rear longitudinal edges of the main part and connecting the front region and the rear region to one another in the put-on state of the disposable incontinence diaper, wherein the side portions are formed as running obliquely in relation to the longitudinal direction, or in a curve-shaped manner, at least at the edges facing the crotch region, in order to form leg cutout regions, and the main part is formed in an hourglass-shaped manner, at least in the crotch region, which comprises the following process steps:

supplying a continuous web of flat material in a longitudinal direction in order to produce portions of material for the forming of the side portions, forming first material clearances along a first cutting line at a side edge of the web of flat material in order to produce contoured cutouts in the web of flat material, an imaginary parallel line, which is parallel to the longitudinal direction and placed at the point P of maximum extent of the cutout transversely in relation to the longitudinal direction, defining an outer sub-region and an inner sub-region of the web of flat material, folding the web of flat material about at least one first folding line running in the longitudinal direction, the folding line running within the outer sub-region, severing longitudinal portions of the folded web of flat material for the respective forming of portions of material, undetachably fixing the portions of material to a respective longitudinal edge of a web for the main part of the diaper for the forming of side portions, forming second material clearances along a second cutting line, the second cutting line taking in the side portions and a respective side edge of the web for the main part of the diaper, and the second cutting line crossing the first cutting line in such a way that the second cutting line does not extend through the first folding line of the front and rear side portions.

The web of flat material forming the later side portions is therefore first provided with first material clearances, which predetermine the contour of outer sub-portions of the later leg opening regions.

Subsequently, the web of flat material is folded at least once, so that, after the severing of longitudinal portions, already pre-folded portions of material are fixed to the web for the main part of the diaper. Only thereafter, that is to say after the fixing of the portions of material to the web for the main part of the diaper, does the second cut take place in order to produce the second material clearances. If this second cut indeed crosses the first cutting line, but does not extend through the first folding line, that is to say as it were starts below the first folding line, it can be reliably avoided that the cut is taken through folding portions and folding lines of the side portions. The pre-folded configuration of the portions of material allows the still unfinished diaper web to be guided reliably and stably in the high-speed diaper machine and subjected to further precision processing. This is attributable particularly to the maximum width B1 of the diaper web to be guided in the region of the side portions being significantly reduced, in particular in relation to the minimum width B2 of the diaper web in the crotch region before the forming of the second material clearances, so that the diaper web can be guided better under tensile stress.

The web for the main part is preferably conveyed in the longitudinal direction at a speed v1 of 100-700 m/min, particularly of 120-550 m/min, more particularly of 130-450 m/min.

This width ratio B1/B2 is preferably more than 1.1, but at most 2, particularly at most 1.8, more particularly at most 1.7, more particularly at most 1.6.

Preferably, the second cutting line extends from a point A on the first cutting line of a rear side portion in a curve inwardly in the direction of the crotch region, initially as far as a point B of a respective rear side edge of the main part and then into the main part, the point A being at a distance from the first folding line inwardly in the transverse direction. After that, the cutting line extends continuously further through the crotch region of the main part and, following that, in a curve outwardly through a point C of the front side edge of the main part and finally as far as a point D on the first cutting line of the front side portions, the point D being at a distance from the first folding line of the front side portions inwardly in the transverse direction.

It has been found to be particularly advantageous if the points A and D are at a distance from the respective first folding line inwardly in the transverse direction of 2-60 mm, particularly 3-50 mm, more particularly 4-40 mm, preferably at most 30 mm, more preferably at most 20 mm, more particularly at most 10 mm and more particularly at most 5 mm.

Preferably, the width of the side portions in the unfolded configuration, that is to say the extent thereof beyond the side edge of the main part of the diaper, is 10-40 cm, particularly 12-30 cm, more particularly 13-25 cm. Preferably, the front side portions thereby have the same width as the rear side portions.

In view of these large dimensions, it has been found to be particularly advantageous if the web of flat material is folded on itself, in particular in a z-shaped manner, about a second folding line, running in the longitudinal direction, the second folding line being arranged closer to the side edge than the first folding line. Particularly preferably, the web of flat material is folded on itself, in particular in a w-shaped manner, about a third folding line, running in the longitudinal direction, the third folding line being arranged closer to the side edge than the second folding line. The first folding line is therefore that folding line that is at the smallest distance from the main part when viewed in the transverse direction. According to a preferred embodiment, the sub-portions of the side portions that are folded on one another are detachably fixed, in particular by ultrasonic welding spots.

The web for the main part, conveyed in the longitudinal direction, preferably comprises a nonwoven material and/or an absorbent pad material and/or a back sheet material. The back sheet material may be, in particular, a film material or a liquid-impermeable nonwoven material or a nonwoven-film laminate.

In a first variant of the process according to the invention, a single web of flat material forming side portions is supplied to the web for the main part. The portions of material severed from this web in such a case form left and right as well as front and rear side portions of the incontinence article.

According to a second variant, two webs of flat material forming side portions are supplied to the web for the main part of the diaper. Preferably, in such a case the one web of flat material forms left side portions and the other forms right side portions. It would also be conceivable for the one web of flat material to form front side portions of the diaper and the other to form rear side portions of the diaper. In such a case, it would also be conceivable and advantageous if the webs of flat material differed with regard to at least one property.

Preferably, the web of flat material is made to produce double blanks, in such a way that two portions of material are obtained from one longitudinal portion of the web of flat material, the first material clearances and the folding of the web of flat material taking place on both sides, that is to say at a first and a second longitudinal edge of the web of flat material, and the web of flat material being divided in the longitudinal direction. In such a case, the web of flat material is preferably divided in the longitudinal direction after the forming of the first material clearances and after the folding of the web of flat material. Furthermore, closure means are preferably applied to the web of flat material before the dividing of the web of flat material.

The portions of material forming side portions severed from the web of flat material may in each case form a single front and/or rear side portion of the diaper. Preferably, however, a portion of material forms two side portions of the diaper. In a particularly preferred embodiment, a portion of material forming two side portions is fastened here to a still continuous web for the main part that is conveyed in the longitudinal direction. According to a preferred embodiment of this variant of the process, in order to form individually separated disposable incontinence diapers, the web for the main part is separated transversely in relation to the longitudinal axis through the portions, that is to say that a separation of the portion of material into two side portions only takes place with the individual separation of the incontinence articles.

It has been found to be advantageous to produce the disposable incontinence diapers here in such a way that, with disposable incontinence diapers conveyed following one another in the longitudinal direction, the rear region of the one disposable incontinence diaper follows on from the rear region of the other disposable incontinence diaper, and the front region of the one disposable incontinence diaper follows on from the front region of the other disposable incontinence diaper. It would also be conceivable and advantageous for the rear region of the one disposable incontinence diaper to follow on from the front region of the other disposable incontinence diaper. According to these two variants of the process, in each case one portion severed from the web of flat material transversely in relation to the longitudinal direction forms side portions of two disposable incontinence diapers conveyed following one another.

The contours of the material clearances may comprise straight portions, in particular running obliquely in relation to the longitudinal direction of the disposable incontinence diaper, and/or curve-shaped portions. In a preferred embodiment, the contour of the material clearances comprises exclusively curve-shaped portions. The minimum curve radius here is preferably at least 5 mm, particularly preferably at least 10 mm. Preferably, the contour of the leg opening regions comprises curve-shaped portions with a different curve radius.

It has also been found to be advantageous to form the front and/or rear side portions from a nonwoven material. Suitable in particular are all nonwoven materials that contain at least one constituent component that is based on a thermoplastic polymer. The nonwovens may contain fibers of PE, PP, PET, rayon, cellulose, PA and mixtures of these fibers. Bicomponent or multicomponent fibers are also conceivable and advantageous. Advantageous in particular are carded nonwovens, spunbonded nonwovens, water-jet needled nonwovens, SM nonwovens, SMS nonwovens, SMMS nonwovens or else laminates of one or more of these types of nonwoven, S standing for spunbonded and M standing for meltblown nonwoven layers. Particularly preferred are spunbonded nonwovens, since they have a high strength in the longitudinal and transverse directions, and consequently can withstand particularly well the shearing forces acting on them as a result of the engagement of mechanical closure aids that may be present. In order to prevent fibers from being torn out from the nonwoven bond during the release of the mechanical closure aids, it is advantageous to provide the nonwoven material component with an embossed pattern, by means of which preferably all the fibers of the nonwoven component are bonded. Advantageous in particular in such a case is a thermally embossed pattern, which is produced particularly advantageously by calendering of the nonwoven material while thermal energy is supplied.

Furthermore, it is found to be advantageous that, laterally alongside the longitudinal edges of the absorbent pad, first elastic elements with a component in the longitudinal direction are joined onto the main part. These elastic elements may run exactly in the longitudinal direction, that is to say in a straight line, or, particularly advantageously, also be provided such that they follow a certain contouring along the leg openings. The elastic elements in such a case take a curved path along the leg opening. In a particular development of this concept of the invention, it is provided that the elastic elements do not extend into the side portions, but are limited to a positioning within the main part. Furthermore, second elastic elements made to extend in the first longitudinal direction, in particular in the form of upright cuff elements, known as such and known per se, for example including from EP0263720A1, may be joined onto the web for the main part of the diaper. These preferably upright second elastic elements flank to a certain extent a center of the main part of the diaper or absorbent pad; they may be provided in the region of the edges of the absorbent pad, within the edges of the absorbent pad or outside the edges of the absorbent pad. They form a lateral run-out guard of the disposable incontinence diaper.

In a further advantageous development of the invention, the side portions have an inner side and an outer side, the rear side portions having closure means with, in particular, mechanical closure aids, and it being possible for the closure means for securing the disposable incontinence diaper as intended on the body of a person to be detachably secured, at least in certain regions, both to the outer side of the rear side portions and to the outer side of the front side portions.

In a development of this concept of the invention, it is provided that the closure means for securing the disposable incontinence diaper as intended on the body of a person can be detachably secured, at least in certain regions, both to the outer side of the main part and to the outer side of the front side portions, the retaining forces between the closure means and the outer side of the front side portions preferably being greater than the retaining forces between the closure means and the outer side of the main part. This also makes the user in most cases secure the closure means to the front side portions.

The outer side of the main part of the disposable incontinence diaper is preferably formed by a nonwoven material, at least in certain regions, but in particular over the full surface area. This imparts a textile-like impression to the disposable incontinence diaper. In such a case, it is advantageous to form the back sheet of the main part from a nonwoven-film laminate, the nonwoven layer coming to lie on the outside and the film layer coming to lie inwardly directed toward the absorbent pad, so that the nonwoven layer forms the outer side of the main part. This on the one hand ensures the liquid-impermeability of the main part and on the other hand ensures the skin-friendly character of the diaper. The film layer of this nonwoven-film laminate is then preferably formed from a one- or multi-layer liquid-impermeable, but preferably nevertheless breathable film, the breathability of the front and/or rear side portions preferably being greater than the breathability of the nonwoven-film laminate forming the back sheet of the disposable incontinence diaper.

Preferably, the rear side portions differ from the front side portions with respect to at least one, particularly at least two, more particularly at least three and more particularly at least four, of their primary properties, selected from the group comprising the type of material, basis weight, breathability, density, stretchability, closure force, areal extent, thickness and color.

Type of material: Particularly if both side portion components are formed from a nonwoven material, it is found to be advantageous if, for example, the front side portions are formed from a softer, more skin-friendly nonwoven material than the rear side portions, since the front side portions are intended to come to lie on the inside when the diaper is put onto the body. Furthermore, it may be advantageous to form the rear side portions from a more tension-resistant material, since the closure means are preferably attached to the rear side portions and strong tensile forces act by way of the closure means on the side portions when the diaper is put on. Preferred differentiations with regard to the type of material can be realized by the type of fiber used, the nonwoven forming process or laminate formations.

Basis weight: The previously mentioned requirements can preferably be achieved, at least in some part, by way of a differentiation of the basis weight, measured in $g/m^2$. Preferably, the basis weight of the front side portions differs from that of the rear side portions by at least 10%, particularly by at least 20% and more particularly by at least 30%. According to a further concept of the invention, the basis weight of the front and/or the rear side portions is preferably 15-60 $g/m^2$, particularly 20-45 $g/m^2$, more particularly 25-40 $g/m^2$ and more particularly 28-35 $g/m^2$.

Breathability: Preferably, the front and/or rear side portions are formed by an air- and/or water-vapor-permeable nonwoven material. Since the subjective perception of the wearing comfort varies from target group to target group (for example bedridden patients versus mobile patients), it may be advantageous to make the breathability either of the front side portions or of the rear side portions greater. Preferably, the breathability, measured as the water vapor transmission rate (WVTR) to DIN 53122-1 (edition: 2001-08) of the front side portions differs from that of the rear side portions by at least 5%, particularly by at least 10% and more particularly by at least 20%. Preferably, the breathability of the front and/or rear side portions is in this case at least 1000 g/m$^2$/24 h, particularly at least 1500 g/m$^2$/24 h, more preferably at least 2000 g/m$^2$/24 h.

Density and thickness: The subjectively perceived softness of the material of the side portions, and consequently a major component of the wearing comfort, can also be advantageously controlled by way of a differentiation of the density and/or thickness of the material. Preferably, the thickness, measured in mm and determined under a test pressure of 0.5 kPa, and/or the density, measured in g/m$^3$ and determined from the variables of the basis weight and thickness of the material, of the front side portions differs from the density and/or the thickness of the rear side portions by at least 15%, particularly by at least 20% and more particularly by at least 25%.

Stretchability: Stretching is understood here as meaning the ratio between an increase in length of a side portion of the disposable incontinence diaper as a result of the effect of a force and the original length. During the use of disposable incontinence diapers of this type, in particular forces in the circumferential direction, that is to say the transverse direction, of the diaper act on the side portions. The property of stretchability consequently means the extent of the stretching of the side portion under the effect of a force in the transverse direction of the diaper. That is to say, the greater the extent of the stretching, the greater the stretchability. Preferably, a rear side portion has a greater stretchability than a front side portion under the effect of the usual force during the use of the diaper. In particular, according to the test method described in DE102005048868A1, a rear side portion stretches more than a front side portion under the effect of a force of 45 N. Preferably, a rear side portion under the effect of a force of 45 N stretches by at least 20%, particularly at least 25% and more particularly at least 30%. On the other hand, under the effect of a force of 45 N, a front side portion stretches only by preferably at most 15%, particularly at most 10% and more particularly at most 8%. Preferably, at least one rear side portion is elastically stretchable, at least in the transverse direction. The stretchability of the side portion is referred to as elastic if, under the brief effect of a force, stretching of at least 40% is possible and, when this force is taken away, an elongation (permanent elongation) of at most 20% remains. In an advantageous development of the invention, the elastic stretchability of a rear side portion in the transverse direction is at least 40%, particularly at least 50%. According to a further concept of the invention, the absolute extent of the elastic stretching of a rear side portion is preferably at least 3 cm, particularly at least 5 cm and more particularly at least 7 cm.

Closure force: The closure force of the side portions is understood as meaning the retaining force between the closure means of the rear side portions and the outer side of the side portions. Preferably, the retaining forces between the closure means and the outer side of the rear side portions are lower here than the retaining forces between the closure means and the outer side of the front side portions. This advantageously has the effect that the user preferably secures the closure means to the front side portions, which significantly benefits the snug fit and wearing comfort of the diaper. The retaining forces mentioned above or below are preferably determined as over-the-stomach retaining forces. The over-the-stomach retaining forces should be determined by the test method described in EP1915977A1. The retaining forces as over-the-stomach retaining forces, determined between the closure means, particularly comprising mechanical closure aids, and the outer side of the front side portions, are preferably 58-90 N/25 mm, particularly 60-80 N/25 mm. The over-the-stomach retaining forces between the closure means, particularly comprising mechanical closure aids, and the outer side of the rear side portions are preferably lower than the over-the-stomach retaining forces between the closure means and the outer side of the front side portions, but they are preferably nevertheless at least 15 N/25 mm, particularly at least 30 N/25 mm.

Preferably, the mechanical closure aids comprise burr hook elements known per se. In a further embodiment, it is provided that at least one closure means, preferably all the closure means, also comprise(s) an adhesive closure aid, in particular a pressure-sensitive adhesive zone, for example such as that disclosed in EP1915977A1.

Areal extent: In a development of the invention, it is found to be advantageous if the rear side portions have a greater areal extent than the front side portions, preferably an areal extent greater by at least 10%, particularly by at least 15%. In particular, the length of the rear side portions, that is to say their extent in the longitudinal direction of the diaper, may be at least 10 cm, particularly at least 15 cm, more particularly at least 18 cm and more particularly at least 22 cm. It has also been found to be advantageous if the length of the rear side portions is at least 10%, particularly at least 15%, more particularly at least 20% and more particularly at least 22% of the overall length of the disposable incontinence diaper. Advantageously, the overall length of the disposable incontinence diaper is 50-120 cm, particularly 60-110 cm and more particularly. 70-110 cm. Furthermore, it is found to be advantageous if the front side portions have a smaller longitudinal extent than the rear side portions, particularly a longitudinal extent that is smaller by at least 5%, more particularly by at least 10%, more particularly by at least 15% and more particularly by at most 50%. In a development of the invention, it is found to be advantageous if the width of the side portions, that is to say the extent of the side portions beyond the side edge of the main part of the diaper, is 10-40 cm, particularly 12-30 cm, more particularly 13-25 cm. Preferably, the front side portions have the same width as the rear side portions.

Color: Finally, it may be advantageous to differentiate the front side portions from the rear side portions with regard to the color. This may also indicate clearly to the users the function of the front side portions as the preferred area for placing the closure means.

Further features, details and advantages of the invention are provided by the appended patent claims and the graphic representation, and by the following description of preferred embodiments of the invention.

In the drawing:

BRIEF DESCRIPTION OF THE DRAWING

FIG. 4 shows an enlarged partial view of the web of flat material represented in FIG. 3 after producing the first material clearance and before folding the web of flat material and FIG. 5 shows a further variant of the production process according to the invention.

DESCRIPTION OF THE PREFERRED EMBODIMENT

Figure 1:
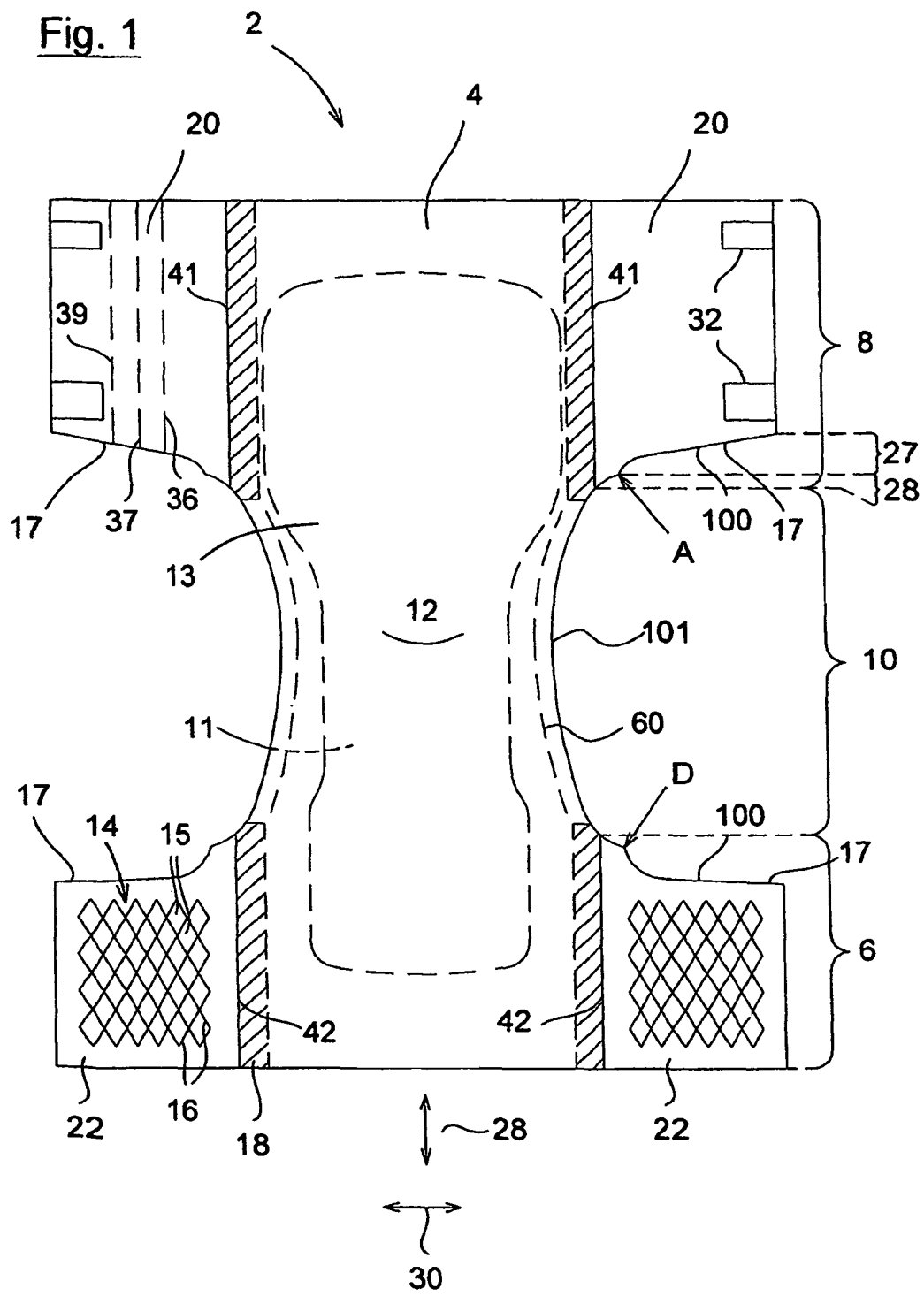
FIG. 1 shows a plan view of the side facing away from the body of a disposable incontinence diaper produced according to the invention
Figure 2:
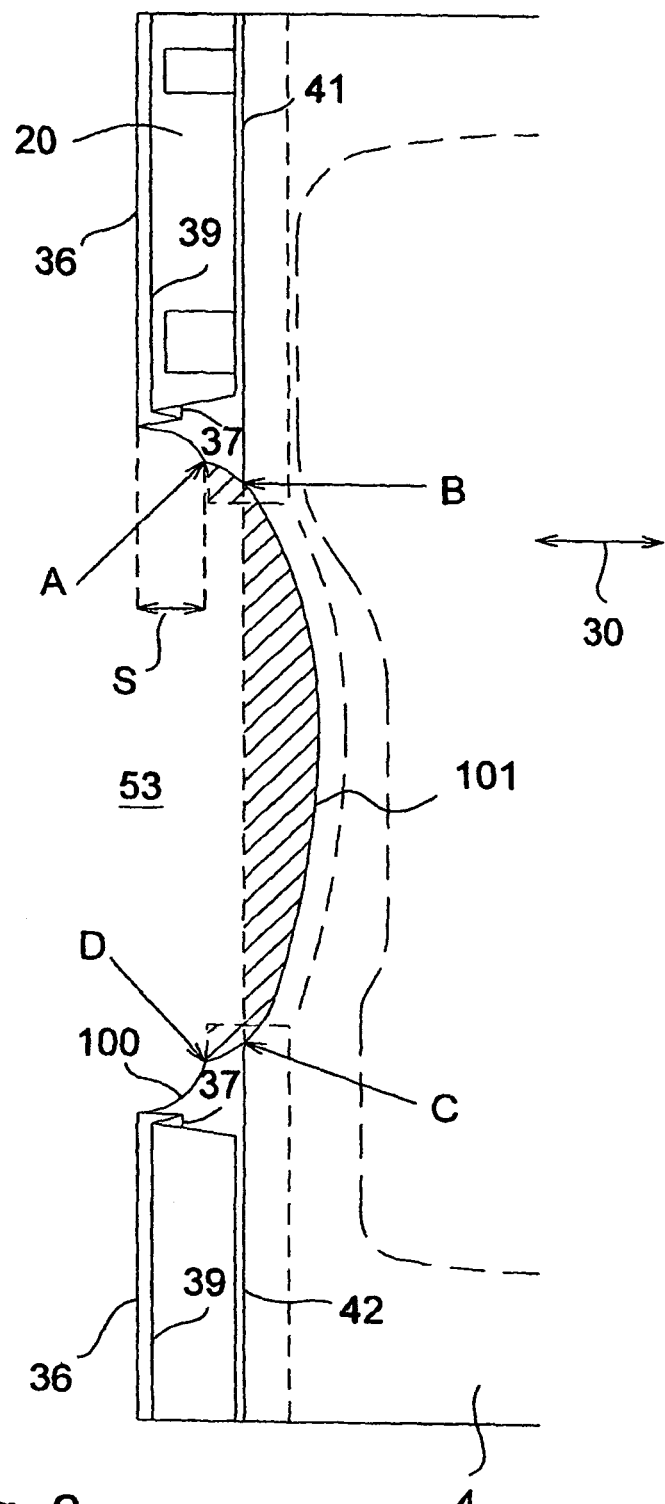
FIG. 2 shows a partial plan view of the side facing away from the body of the disposable incontinence diaper produced according to the invention, as shown in FIG. 1, with still folded side portions

FIG. 1 shows a plan view of the outer side, that is to say the side facing away from the body, of a disposable incontinence diaper 2 of the open type, to be produced in a way according to the invention, in the unfolded configuration. The disposable incontinence diaper 2 comprises a main part 4 with a front region 6, a rear region 8 and a crotch region 10, lying in between in the longitudinal direction. Also indicated is an absorbent pad 12, which is usually arranged between chassis-forming materials of the main part 4, that is to say in particular between a liquid-permeable top sheet 11, formed from a nonwoven material, and a substantially liquid-impermeable back sheet 13, formed from a film material, of the main part 4. The back sheet 13 may also be formed from a liquid-impermeable nonwoven material or a nonwoven-film laminate, the nonwoven layer then coming to lie on the outside and the film layer coming to lie inwardly directed toward the absorbent pad. This imparts a textile-like impression to the disposable incontinence diaper 2. Laterally alongside the longitudinal edges of the absorbent pad 12, first elastic elements 60 are joined onto the main part 4, between the top sheet 11 and the back sheet 13. The elastic elements 60 run substantially in the longitudinal direction, that is to say with a major component in the longitudinal direction, taking a curved path along the portion of the main part 4 that is the leg opening region to be assigned to the crotch region 10. The disposable incontinence diaper 2 further comprises front side portions 22 and rear side portions 20, which are joined as separate components, preferably based on nonwoven material, to the main part 4 on both sides. The side portions 20, 22 are undetachably connected in an overlapping region 18 to chassis-forming materials of the main part 4, that is to say for example to the back sheet 13 and/or the top sheet 11. The side portions 20, 22 extend beyond the front and rear longitudinal edges 42, 41 of the main part in the transverse direction 30. Front and rear longitudinal edges 42, 41 of the main part are understood in the context of the present invention as meaning those longitudinal edge regions of the main part to which the side portions are joined and beyond which they extend. The longitudinal extent of the front and rear side edges of the main part 42, 41 consequently also define the longitudinal extent of the front region 6 and the rear region 8 of the disposable incontinence diaper 2, as FIG. 1 illustrates. In order not to overburden FIG. 1, the position of the first, second and third folding lines 36, 37, 39 has merely been indicated on a rear left side portion 20. FIG. 2, still to be considered in more detail, shows the left half of the diaper with side portions 20, 22 still folded in a w-shaped manner. This folded configuration is then folded about a further folding line, which runs approximately along the longitudinal edge of the main part 4, inwardly onto the side of the main part that is facing the body (not represented), in the ready-to-use configuration.

The side portions 20, 22 are conceived and intended for being connected to one another in the put-on state of the disposable incontinence diaper 2, in order to form a hip region of the sanitary article that is continuous in the circumferential direction. In this case, the side portions 20, 22 provided on one side of the main part 4 are respectively connected to one another. For this purpose, preferably mechanical closure means 32, particularly with mechanical closure aids such as burr hooks, are provided on the rear side portions 20 and can be detachably secured to the outer side of the front and rear side portions 20, 22. Preferably, the closure means can also be detachably secured to the outer side of the main part. At least the outer side of the front side portions has for this purpose an embossed pattern 14, which is only schematically indicated in FIG. 1. The joining regions produced by hot calender embossing are formed by a multiplicity of lines, to be specific by two groups of lines running respectively in parallel within a group, the lines of the one group intersecting with the lines of the other group at an angle of 33 degrees to form a regular rhomboid pattern, so that rhomboidal loop regions 15 that are arranged in the manner of islands and are connected are surrounded by linear joining regions 16. The lines forming joining regions 16 have in the case represented a width of 1.0 mm and an embossing depth of 0.6 mm. The distance between two neighboring parallel-running lines of the two groups of lines is 4.7 mm. The embossed area, that is to say the sum of the area of all the joining regions 16 with respect to the overall area of the embossed pattern (joining regions+loop regions), is 32%. The closure means 32 of the rear side portions 20 can be reliably brought into engagement with these loop regions 15. The over-the-stomach retaining forces between the closure means 32 and the outer side of the front side portions 22 is preferably at least 58 N/25 mm. Both the front side portions 22 and the rear side portions 20 are formed from a nonwoven material, in the case represented from a PP spunbonded nonwoven. The basis weight of the nonwoven material of the front side portions is 30 g/m$^2$. The fiber thickness of the fibers forming the nonwoven material is 2 dtex.

As can be seen from FIG. 1, the rear side portions 20 also have a greater areal extent than the front side portions 22.

Front and rear side portions 20, 22 have at their edges 17 facing the crotch contoured leg cutout regions. The contoured leg cutout regions of the side portions 20, 22 have for their part an outer sub-portion 27 and an inner sub-portion 28. The outer sub-portion 27 extends from a respective outer longitudinal edge of the side portions as far as a point A (in the case of the rear side portions 20) or as far as a point D (in the case of the front side portions 22). The region following on from these points A and D respectively in the direction of the main part 4 forms the respective inner sub-portion 28. This then goes over unvaryingly into the respective leg cutout region of the main part 4. The points A and D respectively represent to a certain extent a point of slight variability of the otherwise unvarying, particularly curve-shaped, contouring of the leg cutout regions. This design of the leg cutout regions of the side portions is brought about by the production process according to the invention, which is described in more detail below and comprises the forming of first and second material clearances along first 100 and second cutting lines 101.

Figure 3:
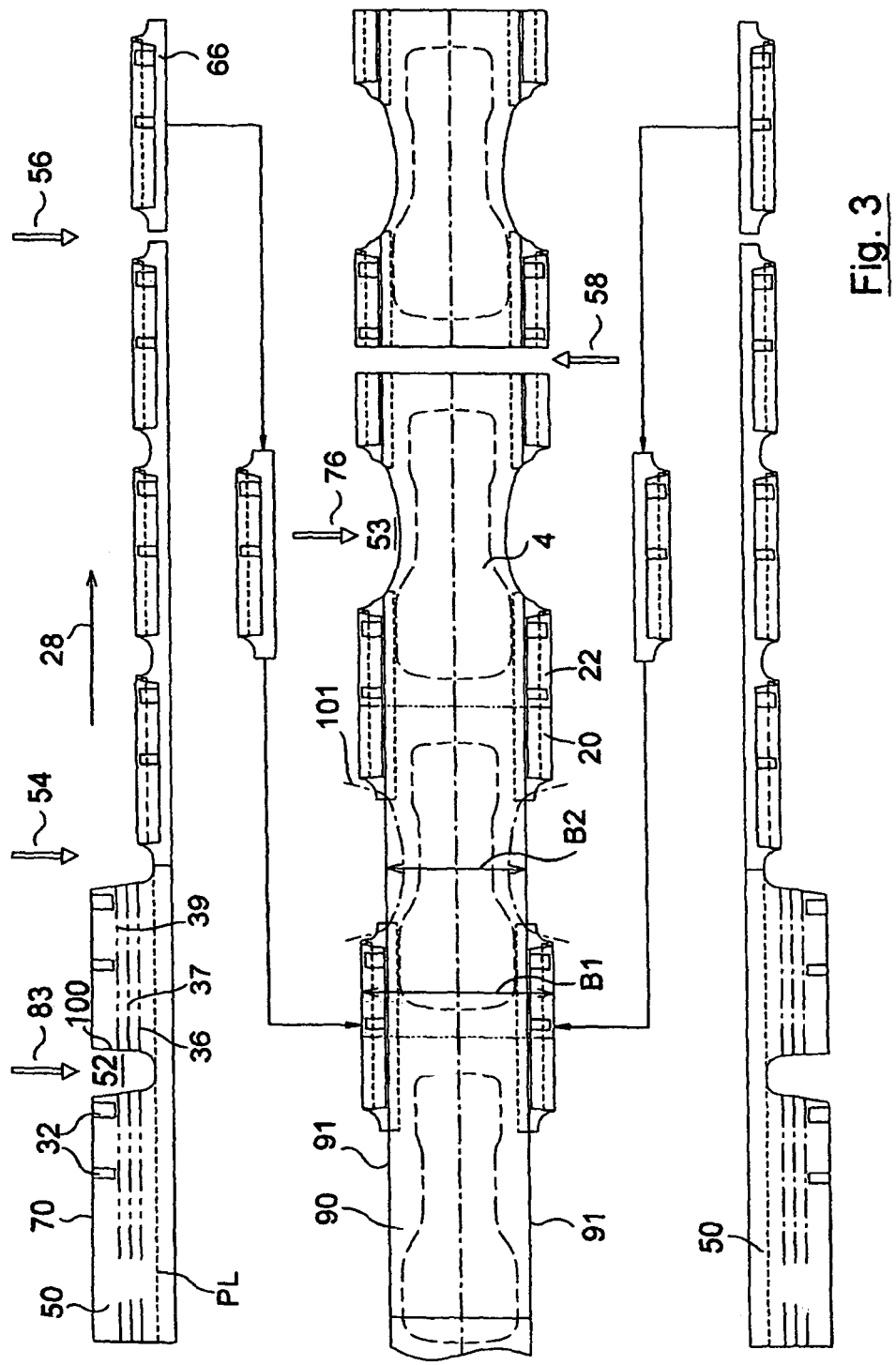
FIG. 3 shows a schematic representation of a production process according to the invention
Figure 4:
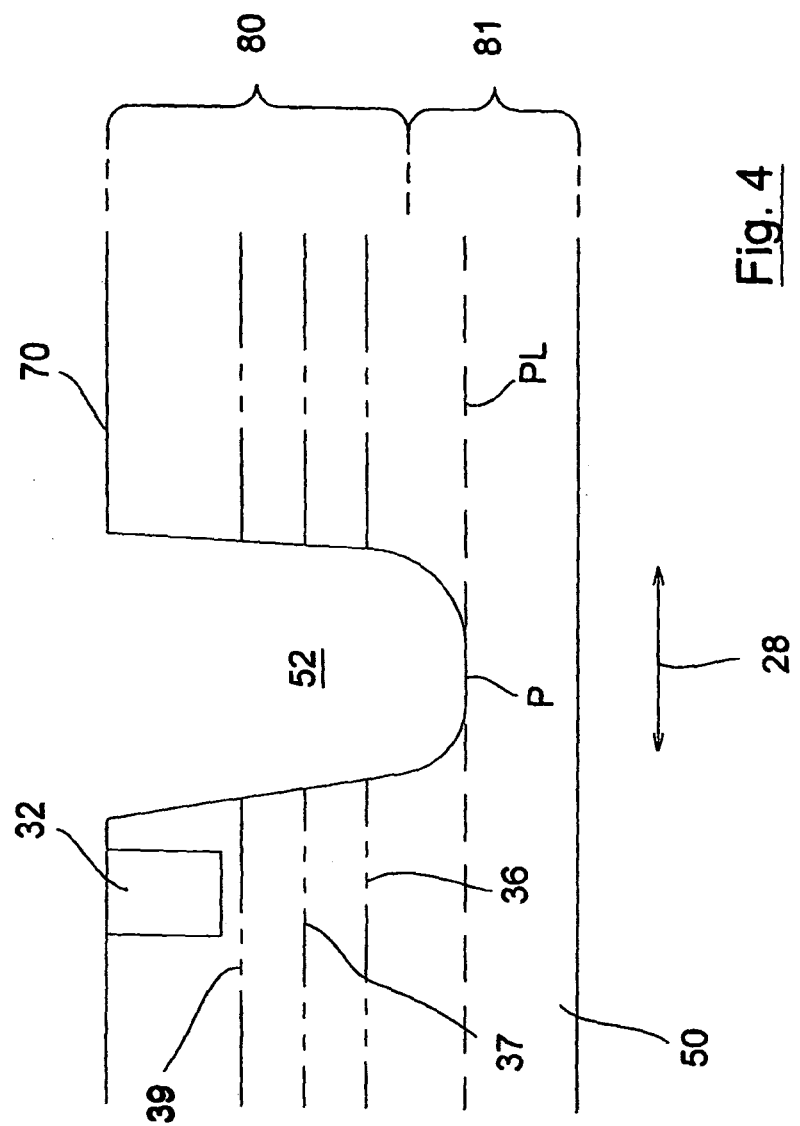

It is found to be advantageous for the production of this diaper 2 if a web of material forming the side portions 20, 22 is supplied continuously in the longitudinal direction. A process according to the invention that can be used for this is now described on the basis of FIG. 3:

FIG. 3 schematically shows the supplying and configuring of two webs of flat material 50, from which the left and right, front and rear side portions 20, 22 of the diaper 2 are formed. The webs of flat material 50 are conveyed in the longitudinal direction 28 (longitudinal production). In order to form a sub-portion of the later contouring of the side portions 20, 22 on the side thereof facing the crotch region 10, the first material clearances 52 are formed along a first cutting line 100 at a respective side edge 70 of the webs of flat material 50 by means of a separating tool, preferably a rotating cutter roller, at a first cutting station 83. FIG. 4 shows an enlarged partial view of a web of flat material 50 provided with the material clearance 52. It can be seen that an imaginary parallel line PL, which is parallel to the longitudinal direction 28 and placed at the point P of maximum extent of the cutout transversely in relation to the longitudinal direction 28, defines an outer sub-region 80, in which the material clearances 52 are arranged, and an inner sub-region 81 of the web.

Before or after the forming of the material clearances 52, closure means 32 are applied between two openings 52 following one another in the direction of production. These are adhesively and/or mechanically attaching closure means 32 known per se, for example in the form of strip-shaped closure tapes.

In a folding station 54, the web of flat material 50 is folded on itself from the outside about three folding lines 36, 37, 39 running in the longitudinal direction 28, so that a w-shaped folding is obtained. In this respect, it is provided according to the invention that the first folding line 36, that is to say the folding line lying furthest inward, runs within a respective outer sub-region 80. The second folding line 37 is arranged closer to the side edge 70 than the first folding line 36, and the third folding line 39 is arranged closer to the side edge 70 than the second folding line 37. Consequently, the further folding lines 37, 39 also run within the outer sub-region 80. If required, the sub-portions of the web of flat material folded on one another are detachably fixed to one another.

In a respective individual separating station 56, the webs of flat material 50, which are still continuous in relation to the longitudinal direction, are separated transversely in relation to the longitudinal direction 28 into portions of material 66. The separation preferably takes place in the region of maximum extent of the cutout forming the first material clearance, transversely in relation to the longitudinal direction. These portions of material 66 are then applied to the web for the main part 90, likewise conveyed in the longitudinal direction, and undetachably fastened there, in the folded state as described above, to longitudinal edge portions of the later main part 4 of the diaper in order to form side portions 20, 22. The still continuous diaper web then has in the region of the folded side portions a maximum width B1 (extent transverse to the longitudinal direction 28) of 510 mm; in the crotch region, the minimum width B2 is 330 mm. The ratio of the widths in the case represented is therefore 1.55, and is consequently small enough for the still unfinished diaper web to be reliably and precisely further conveyed and further processed at continuing high speed.

Severing the portions of material 66, supplying them to the web for the main part 90 and subsequently joining the portions of material 66 to both side edges of the web for the main part 90 preferably takes place by means of devices that are known per se to a person skilled in the art, are not represented in FIG. 3 and are known as slip-cut or else cut-and-place units.

The portions of material 66 schematically represented in FIG. 3, after severing from the continuous webs of flat material 50, may be a side portion to be assigned to a single diaper. However, as represented in FIG. 3, it is advantageous that this portion of material forms side portions of two diapers conveyed following one another in the longitudinal direction 28 or direction of production. In the latter case, the side portions are then preferably and expediently severed from a continuous web, as described further below, likewise transversely in relation to the longitudinal direction, with the final individual separation of the diapers at an individual separating station. It can be seen that portions of material 66 for forming side portions 20, 22 are joined onto a continuous web 90, which forms the main parts 4 of the diaper. Each portion of material 66 respectively comprises the side portions 20, 22 of two diapers conveyed following one another in the longitudinal direction 28 or direction of production. In the case of the process according to FIG. 3, the diapers are produced in such a way that, with diapers conveyed following one another in the longitudinal direction 28, the rear region 8 of the one diaper follows on from the front region 6 of the other diaper.

It would also be conceivable and advantageous for up to four of the webs of flat material represented in FIG. 3 to be implemented in a production process of a diaper, a respective web of flat material then being able to provide rear or front left side portions or rear or front right side portions. In this way, different web materials can also be used for forming the side portions in the front region and in the rear region.

In a subsequent process step, likewise represented in FIG. 3, at a further respective second cutting station 76, the two material clearances 53 are formed along a second cutting line 101, the second cutting line 101 taking in the side portions 20, 22 and a respective longitudinal edge 91 of the web for the main part 90 of the diaper, and the second cutting line 101 crossing the first cutting line 100 in such a way that the second cutting line does not extend through the first folding line of the side portions 20, 22.

This second material clearance 53 gives the leg opening contour its final form. In FIG. 3, the profile of the second material clearance taking form in this process step is schematically indicated as a dashed second cutting line 101 on the diaper directly upstream of the cutting station 76. The path of this cutting line 101 can also be seen in detail in FIG. 2: the second material clearances 53 are formed along a second cutting line 101, which extends from a point A on the first cutting line 100 of a rear side portion 20, that is to say from the point at which the cutting lines 100, 101 cross for the first time, in a curve inwardly in the direction of the crotch region 10 initially as far as a point B of a rear side edge 41 of the main part 4 and then into the main part 4. The second cutting line 101 then extends further through the crotch region 10 along the longitudinal edge of the main part 4, preferably without taking in the elastic elements 60 and the absorbent pad 12, and then subsequently in a curve outwardly through a point C of the front side edge 42 of the main part 4, and finally as far as a point D on the first cutting line 100 of the front side portion 22, that is to say as far as the point at which the cutting lines 100, 101 cross once again. The described path of the cutting line 101 does not have to mean that the process step of cutting out must actually begin at the point A. The cutting operation itself may of course also begin at point D and then continue via point C, and B to point A. The cut could also start at any other desired point on the described cutting line 101 and then continue along the cutting line in both directions. In any case, the path of the cutting line 101 described with reference to FIG. 2 is ultimately obtained. Point A and point D are at the distance S, to be precise 4-10 mm, from the respective first folding line 36 inwardly in the transverse direction 30, that is to say in the direction of the main part 4 of the diaper 2, so that the second cutting line 101 does not take in the respective first folding line 36 of the side portions 20, 22. The further folding lines 37, 39 of the side portion 20 are also not taken in by the second cutting line 101. The cut-out material components of the side portions 20, 22 and of the main part 4 are shown shaded in FIG. 2. This results in the contour described with reference to FIG. 1 of the leg cutout regions with inner and outer sub-portions 27, 28 in the region of the side portions 20, 22 and a leg cutout region lying in between of the main part 4.

Finally, at a diaper individual separating station 58 (FIG. 3), the individual separation of the previously still continuous diaper web takes place transversely in relation to the longitudinal direction, the side portions being separated for the first time into front and rear side portions 20, 22 at the same time as the individual separating cut.

As shown in FIG. 5, it is conceivable and advantageous for a web of flat material 50a to be made to produce double blanks, in such a way that two portions of material 66a are obtained from one longitudinal portion 57 of the web of flat material 50a, the first material clearances 52 and the folding of the web of flat material taking place on both sides, that is to say at a first 70a and a second longitudinal edge 70b, and the web of flat material 50a being divided in the longitudinal direction at a separating station 92 even before portions of material 66a are severed from the sub-webs 50a1, 50a2 thereby obtained. In such a case, as represented in FIG. 5, the one sub-web could be used for forming right side portions and the other sub-web could be used for forming left side portions. Here, the web of flat material may be divided in the longitudinal direction after the forming of the first material clearances and after the folding of the web of flat material, as represented, or already in a preceding process step. To the extent to which the same reference signs as in FIGS. 3 and 4 have been used in FIG. 5, they identify analogous components.

The way in which the process is conducted according to the invention achieves the effect that the still unfinished diaper web with already joined-on side portions can be reliably and stably guided and processed in the high-speed diaper machine. This constitutes a significant improvement of the production process.

I claim:

1. A method for producing an open type disposable diaper, the diaper comprising a main part having a front region with front lateral longitudinal edges, a rear region with rear lateral longitudinal edges and a crotch region, disposed, in a longitudinal direction, between the rear region and the front region, the crotch region subsequently lying between legs of a user, the main part also comprising an absorbent pad, and with rear side portions, joined to the rear region on both sides thereof as well as front side portions, joined to the front region on both sides thereof, the rear and front side portions extending in a transverse direction beyond the front and rear lateral longitudinal edges of the main part to facilitate connection between the front region and the rear region when the diaper is in use, wherein, at least at edges thereof facing the crotch region, the front and rear side portions travel obliquely or in a curve-shaped manner relative to the longitudinal direction in order to form leg cutout regions, the main part being formed, at least in the crotch region, in an hourglass-shaped manner, the method comprising the steps of:
a) supplying a continuous side portion web of flat material in a longitudinal direction;
b) forming first material clearances along a first cutting line at a side edge of the side portion web of flat material to produce contoured cutouts therein, wherein an imaginary parallel line PL, which is parallel to the longitudinal direction and intersects a point P of maximum extent of the contoured cutouts transverse to the longitudinal direction, defines an outer sub-region and an inner sub-region of the side portion web of flat material;
c) folding the side portion web of flat material about at least one first folding line running in the longitudinal direction, the first folding line extending within the outer sub-region;
d) severing longitudinal portions of the folded side portion web of flat material to form individual side portions of material;
e) permanently fixing the individual side portions of material to a respective longitudinal edge of a main part web, thereby forming the front and rear side portions of the diaper on the diaper main part; and
f) forming second material clearances along a second cutting line, the second cutting line intersecting the front and rear side portions as well as a respective longitudinal edge of the main part web; wherein the second cutting line crosses the first cutting line but does not extend through the first folding line of the front and rear side portions.

2. The method of claim 1, wherein the second cutting line extends from a point A on the first cutting line of a rear side portion in a curve inwardly towards the crotch region up to a point B of a respective rear side edge of the main part and then into the main part, the point A being at a distance from the first folding line inwardly in the transverse direction, the second cutting line extending further through the crotch region of the main part and subsequently curving outwardly through a point C of the front side edge of the main part up to a point D on the first cutting line of the front side portions, wherein the point D is at a distance from the first folding line of the front side portion, inwardly in the transverse direction.

3. The method of claim 2, wherein point A is at a distance from the first folding line inwardly in the transverse direction of 2-60 mm.

4. The method of claim 2, wherein point D is at a distance from the first folding line inwardly in the transverse direction of 2-60 mm.

5. The method of claim 1, wherein the side portion web of flat material is folded on itself about a second folding line running in the longitudinal direction, the second folding line being arranged closer the side edge than the first folding line.

6. The method of claim 5 wherein the side portion web of flat material is folded onto itself in a z-shaped manner.

7. The method of claim 5, wherein the side portion web of flat material is folded on itself about a third folding line, running in the longitudinal direction, the third folding line being arranged closer to the side edge than the second folding line.

8. The method of claim 7, wherein the side portion is folded on itself in a w-shaped manner.

9. The method of claim 1, wherein sub-portions of the side portion web of flat material that are folded on one another are detachably fixed.

10. The method of claim 1, wherein the side portion web of flat material is structured to produce double blanks, wherein two portions of material are obtained from one longitudinal portion of the side portion web of flat material, the first material clearances and folding of the side portion web of flat material thereby taking place on both sides at a first and a second longitudinal edge of the side portion web, the side portion web of flat material being divided in the longitudinal direction.

11. The method of claim 10, wherein the side portion web of flat material is divided in the longitudinal direction after forming the first material clearances and after the folding of the side portion web of flat material.

12. The method of claim 1, further comprising applying closure means to the side portion web of flat material.

13. The method of claim 1, wherein the disposable diapers are produced in such a way that, with diapers conveyed following one another in the longitudinal direction, the rear region of one diaper follows on from the rear region of an other diaper and a front region of one diaper follows on from a front region of an other diaper.

14. The method of claim 1, wherein the disposable diapers are produced in such a way that, with diapers conveyed following one another in the longitudinal direction, the rear region of one diaper follows on from the front region of an other diaper or the front region of the one diaper follows on from the rear region of an other diaper.

15. The method of claim 1, wherein a portion of material severed transversely relative to the longitudinal direction forms side portions of two successive diapers.

16. The method of claim 1, wherein side portions of the front region and the rear region are formed differently.

17. The method of claim 1, wherein, subsequent to permanent fixing of the portions of material to a respective longitudinal edge of the main part web, a ratio of a maximum width of the main part web with front and rear side portions to a minimum width of the main part web in the crotch region, before forming the second material clearances, is at least 1.1 and at most 2.

* * * * *